United States Patent [19]
Kogure et al.
[11] 3,959,349
[45] May 25, 1976

[54] 2-HYDROXY-3(4-ALKYLPHENYL)-3-BUTENOIC ACID ESTER AND PROCESS FOR THE PRODUCTION THEREOF

[75] Inventors: Katsura Kogure, Kawagoe; Hiroyasu Koyama, Ohi; Kunio Nakagawa, Kawagoe, all of Japan

[73] Assignee: Nisshin Flour Milling Co., Ltd., Tokyo, Japan

[22] Filed: Nov. 22, 1974

[21] Appl. No.: 526,304

Related U.S. Application Data

[62] Division of Ser. No. 436,632, Jan. 25, 1974, Pat. No. 3,927,084.

[30] Foreign Application Priority Data

Jan. 29, 1973 Japan ............ 48-11164
Jan. 29, 1973 Japan ............ 48-11165

[52] U.S. Cl. ............ 260/473 A
[51] Int. Cl.[2] ............ C07C 69/88
[58] Field of Search ............ 260/473 A

[56] References Cited

UNITED STATES PATENTS

| | | | |
|---|---|---|---|
| 3,259,649 | 7/1966 | McClure | 260/473 A |
| 3,678,093 | 7/1972 | Morita et al. | 260/473 A |

*Primary Examiner*—Paul J. Killos
*Attorney, Agent, or Firm*—James C. Haight

[57] ABSTRACT

A new process for the production of a 2-(4-alkylphenyl)-propionic acid known as a valuable anti-inflammatory agent is now provided, which comprises treating an alkyl 2-hydroxy-3-(4-alkylphenyl)-3-butenoate, a new compound, with an alkali metal alcoholate in an alcohol to give the corresponding alkyl 3-methyl-3-(4-alkylphenyl)-pyruvate, also a new compound, which is then hy drolysed to liberate the corresponding 3-methyl-3-(4-alkylphenyl)-pyruvic acid, and then oxidising the liberated pyruvic acid compound to the desired 2-(4-alkylphenyl)-propionic acid. This new process is operable in a facile way with a high yield of the desired product and is much suitable for a commercial practice than the prior art methods.

2 Claims, No Drawings

2-HYDROXY-3(4-ALKYLPHENYL)-3-BUTENOIC ACID ESTER AND PROCESS FOR THE PRODUCTION THEREOF

This is a division of application Ser. No. 436,632, filed Jan. 25, 1974, now U.S. Pat. No. 3,927,084.

This invention relates to a new process for the production of a 2-(4-alkylphenyl)-propionic acid.

2-(4-Lower alkylphenyl)-propionic acids and their pharmaceutically acceptable derivatives are known to have a high anti-flammatory activity and have widely been used in the treatment of diseases caused by inflammation, such as rheumatism.

Of the 2-(4-alkylphenyl)-propionic acids, 2-(4-isobutylphenyl)-propionic acid is most useful for the therapeutic purpose.

It is known that the synthesis of a 2-(4-alkylphenyl)-propionic acid of the formula (I):

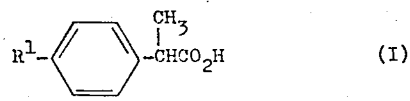

where $R^1$ stands for a lower alkyl group of 2–4 carbon atoms can be conducted by various methods described in the specifications of Japanese Pat. Nos. 7491/65, 22297/68 and 24550/72. However, all these prior art methods suffer from some drawback and are not very suitable for the production of the 2-(4-alkylphenyl)-propionic acid in a commercial scale.

Thus, according to the method of the Japanese Pat. No. 7491/65 (British Pat. No. 971,700) a 4-alkylacetophenone of the formula (VI):

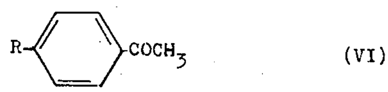

where R stands for an alkyl group is used as a starting material and is converted into the described product, namely the 2-(4-alkylphenyl)-propionic acid of the formula (I) via six reaction stages. This known method involves the many stages of reaction and is not advantageous for the commercial production of the desired compound of the formula (I).

According to the method of Japanese Pat. No. 22297/68 (British No. 971,700) a 4-alkylphenylethane derivative of the formula (VII):

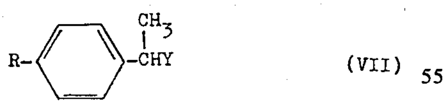

where R stands for an alkyl group and Y stands for a nitrile radical or a carboxylic acid ester radical is hydrolysed to give a corresponding 2-(4-alkylphenyl)-propionic acid of the formula (I). This known method suffers from a drawback that the starting compound of the formula (VII) is difficult to be prepared and hence is very expensive.

According to the method of Japanese Pat. No. 24550/72 (British Pat. No. 1,160,725) a glycidic ester of the formula (IV):

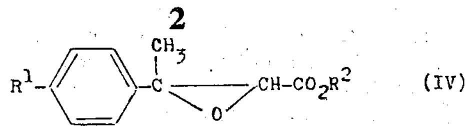

where $R^1$ represents an alkyl group of 2–4 carbon atoms and $R^2$ represents an alkyl group of 1–4 carbon atoms is used as the starting compound and is hydrolysed in the presence of an alkali metal hydroxide to given an alkali metal glycidate of the formula (VIII):

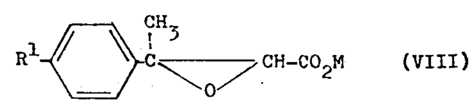

wherein $R^1$ has the same meaning as set out above and M represents an alkali metal, which is, in turn, treated with an acid to produce a propionaldehyde derivative of the formula (IX):

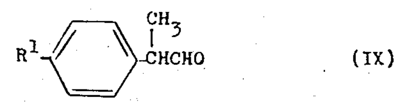

wherein $R^1$ has the same meaning as described above. The propionaldehyde derivative of the formula (IX) is then oxidised to yield the final product, namely the 2-(4-alkylphenyl)-propionic acid of the formula (I). This known method is not suitable for the commercial production of the aimed product (I) because the intermediate product of the formula (VIII) is instable and gives the compound of the formula (IX) only in a low yield so that the overall yield of the final product (I) is poor in this method.

An object of this invention is to provide a new process for the production of 2-(4-alkylphenyl)-propionic acids which can be operated in a facile way and give the desired product in a high yield and which is well suitable to be carried out in a commercial scale. Further object of the invention is to provide new substances which are useful as a starting material or intermediate product for the production of the 2-(4-alkylphenyl)-propionic acids. Another objects of this invention will be clear from the following description.

We have made our extensive research to achieve the above-mentioned purposes. As a result of our research, we have now found that when a 3-methyl-3-(4-alkylphenyl)-glycidic acid alkyl ester of the formula (IV):

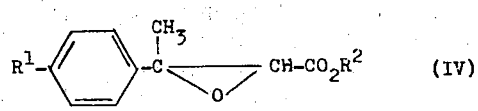

wherein $R^1$ and $R^2$ have the same meaning as defined in the above is treated with a Lewis acid in an aprotoic polar solvent such as dimethylsulfoxide, dimethylformamide and isopropyl ether, there is formed a new substance, a 2-hydroxy-3-(4-alkylphenyl(-3-butenoic acid ester of the formula (II):

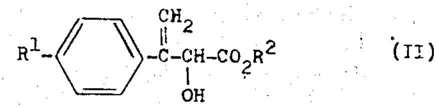

wherein $R^1$ and $R^2$ have the same meanings as described above in a high yield, and that this 2-hydroxy-3-(4-alkylphenyl)-3-butenoic acid ester of the formula (II) may advantageously be employed as a starting compound for the production of the 2-(4-alkylphenyl)-propionic acid of the formula (I). We have further found that when the 2-hydroxy-3-(4-alkylphenyl)-3-butenoic acid of the formula (II) is treated with an alkali metal alcoholate in a lower aliphatic alcohol, it is converted into the corresponding phenylpyruvate of the formula (X):

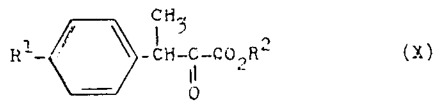

wherein $R^1$ and $R^2$ have the same meanings as described in the above, which is a new substance, too, and which is easily hydrolysable to the corresponding 3-methyl-3-(4-alkylphenyl)-pyruvic acid which is, in turn, oxidisable to the corresponding 2-(4-alkylphenyl)-3-propionic acid of the formula (I). The conversion of the 2-hydroxy-3-hydroxy-3-substituted -3-butenoic acid ester into the corresponding 3-substituted pyruvate (a keto acid) through the treatment with an alkali metal alcoholate is a new reaction, as this is not disclosed in any literature as far as we are aware of.

According to a first aspect of this invention, therefore, there is provided a process for the production of a 2-(4-alkylphenyl)-propionic acid of the formula (I):

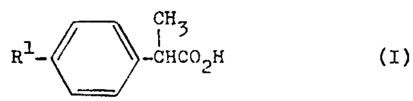

wherein $R^1$ stands for an alkyl group of 2–4 carbon atoms, or a pharmaceutically acceptable salt thereof, which comprises treating a 2-hydroxy-3-(4-alkylphenyl)-3-butenoic acid ester of the formula (II):

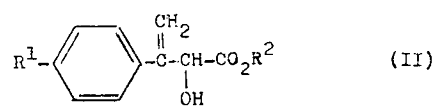

wherein $R^1$ has the same meaning as defined above and $R^2$ stands for an alkyl group of 1–3 carbon atoms with an alkali metal alcoholate in an alcohol to give the corresponding 3-methyl-3-(4-alkylphenyl)-pyruvate, hydrolysing this pyruvate to produce the 3-methyl-3-(4-alkylphenyl)-pyruvic acid of the formula (III):

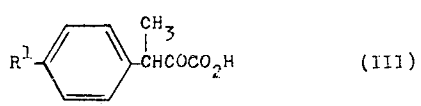

wherein $R^1$ has the same meaning as defined above or a salt thereof, and then oxidising the pyruvic acid compound of the formula (III) or its salt to give the desired 2-(4-alkylphenyl)-propionic acid of the formula (I) or its salt.

It the 2-(4-alkylphenyl)-propionic acid of the formula (I) is yielded in the form of the free acid as the final product of the process, the process of this invention may comprise further converting this free acid into the corresponding pharmaceutically acceptable salt (carboxylate) by reacting with a pharmaceutically acceptable inorganic base such as a sodium or potassium base or a calcium or magnesium base. If the 2-(4-alkylphenyl)-propionic acid of the formula (I) is yielded in the form of its salt (the carboxylate) as the final product of the process, the process of this invention may comprise converting this salt into the free acid form by acid hydrolysis in a known manner.

In the process of this invention, the first reaction step, the second (hydrolysis) step and the third (oxidation) step of the process may proceed with a high efficiency, and the intermediate products from the first and second steps are stable and easy to be purified. In addition, all the reaction steps of the process for producing the final product of the formula (I) from the starting compound (II) may be conducted in one and the same reaction vessel without isolation of the intermediate product and without difficulty, so that the process of this invention may be worked out in a facile way and is very advantageous as a commercial process of producing the 2-(4-alkylphenyl)-propionic acid.

In the first step of the process according to this invention, the starting compound of the formula (II) may be treated with an alkali metal alcoholate in an alcohol in such a manner that the starting compound (II) is taken up into a solution of an alkali metal alcoholate in an alcohol, preferably a lower aliphatic alcohol of 1–4 carbon atoms and the solution is then heated at an elevated temperature. Suitable alkali metal alcoholates are sodium or potassium alcoholate which is derived from a lower alkanol of 1–4 carbon atoms such as methanol ethanol, isopropanol, tertiary butanol and the like. The alkali metal alcoholate may be used in the form of its solution in a lower alkanol of 1–4 carbon atoms such as methanol, ethanol, isopropanol or tertiary butanol which forms the reaction medium. The reaction temperature for the first step may preferably be in a range of 60°–90°C or thereabout, and the reaction duration may suitably be in a range of 30 minutes to 1 hour.

After the reaction of the first step is completed, the reaction mixture may be distilled to remove the alcohol which was served as the reaction medium. The residue is then extracted with ethyl ether. When the resulting ether extract is evaporated to remove the solvent, there is isolated the pyruvate of the formula (X):

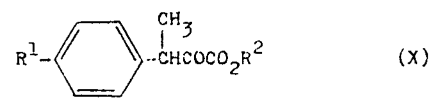

wherein $R^1$ is a lower alkyl group of 2–4 carbon atoms and $R^2$ is a lower alkyl group of 1–3 carbon atoms as defined in the above.

Hydrolysis of this isolated pyruvate product of the formula (X) gives the 3-methyl-3-(4-alkylphenyl)-pyruvic acid of the formula (III) or its salt in the second (hydrolysis) step of the process which is preferably carried out in alkaline conditions. The hydrolysis of the pyruvate product of the formula (X) to form the pyruvic acid product of the formula (III) takes place easily, and it is not necessary to isolate the pyruvate product of the formula (X) from the reaction mixture. Thus, it is feasible without difficulty to carry out the hydrolysis step in such a manner that water is added directly to the reaction mixture from the first step of the process and the mixture is then heated for 10 to 30 minutes under reflux. In this case, the hydrolysis of the pyruvate of the formula (X) takes place in alkaline conditions due to the presence of an alkali metal hydroxide which is formed in situ from the interaction of the alkali metal alcoholate with the water added, and the hydrolysis product is then formed in the form of an alkali metal salt of the pyruvic acid of the formula (III) which may readily be converted into the free acid form by rendering the reaction mixture weakly acidic by addition of hydrochloric acid or sulfuric acid.

The pyruvic acid product of the formula (III) may be isolated from the reaction mixture of the second (hydrolysis) step of the process in such a manner that the reaction mixture is distilled under reduced pressure to remove the solvent, the residue is extracted with water and the aqueous extract so obtained is weakly acidified by addition of hydrochloric acid, followed by extraction with ethyl ether. The pyruvic acid product isolated in this way is of high purity and may be employed as such in the subsequent step of the process.

In the third step of the process, the pyruvic acid product of the formula (III) is oxidised to the desired 2-(4-alkylphenyl)-propionic acid. This oxidation step may conveniently be carried out in such a manner that the pyruvic acid compound of the formula (III) is reacted with hydrogen peroxide in solution in water under alkaline conditions which may be provided by the presence of an alkali metal hydroxide such as sodium hydroxide or potassium hydroxide added. When hydrogen peroxide is used as the oxidising agent, the oxidation step of the process may suitably be carried out at a reaction temperature of 10°–25°C for a reaction time of 10–20 hours. When the oxidation step of the process is carried out using hydrogen peroxide in the presence of an alkali metal hydroxide, the 2-(4-alkylphenyl)-propionic acid of the formula (I) as the oxidation product is formed as an alkali metal salt (carboxylate) thereof. This salt may readily be converted into the free acid form by treating with a mineral acid such as hydrochloric acid or sulfuric acid if necessary. The final product of the formula (I) which is produced according to the process of this invention is of a high purity, and it may easily be purified, if desired, by recrystallisation from petroleum benzine. Furthermore, the 2-(4-alkylphenyl)-propionic acid of the formula (I) in the free acid form may be converted into its pharmaceutically acceptable inorganic salt (carboxylate) such as sodium, potassium or calcium salt or into its pharmaceutically acceptable addition-salt with an organic base such as benzylamine and triethylamine.

In operating the process of this invention, the first, second and third steps of the process may be effected in a single reaction vessel, and the operation of the process is very facile and the process of this invention gives the 2-(4-alkylphenyl)-propionic acid in a high yield. Accordingly, the process of this invention is very advantageous as a commercial process.

2-Hydroxy-3-(4-alkylphenyl)-3-butenoic acid ester of the formula (II) which is employed as the starting compound in the process of this invention may be prepared, for example, in the following way:
Thus, an acetophenone derivative of the formula (IX):

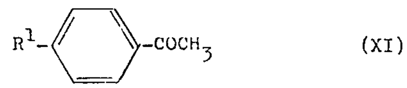

wherein $R^1$ is an alkyl group of 2–4 carbon atoms as described in the above is reacted with an α-haloacetic acid ester of the formula (XII):

$$XCH_2CO_2R^2 \qquad (XII)$$

wherein $R^2$ is an alkyl group of 1–3 carbon atoms and X is a halogen atom, particularly chlorine and bromine to produce the glycidic ester of the formula (IV):

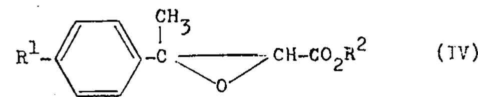

wherein $R^1$ and $R^2$ have the same meanings as defined above. The reaction of the acetophenone derivative of the formula (XI) with the α-haloacetate of the formula (XII) may be carried out according to a known method of Darzen's condensation. The group $R^2$ may conveniently be methyl, ethyl or isopropyl. The condensation reaction may preferably be carried out in an inert atmosphere and under anhydrous conditions in the presence of an alkaline condensation catalyst which may be sodium amide or a sodium alkoxide such as sodium methoxide, sodium ethoxide, sodium isopropoxide and the like.

When the glycidic ester of the formula (IV) so obtained is treated with a Lewis acid such as boron trifluoride or aluminum chloride in an aprotoic polar solvent such as dimethylsulfoxide, dimethylformamide or isopropylether, there is formed the 2-hydroxy-3-(4-alkylphenyl)-3-butenoic acid ester of the aforesaid formula (II) in a high yield. Lewis acid available for this purpose may preferably be boron trifluoride, boron trifluoride etherate or aluminum chloride and may preferably be used at least in equi-molar proportion to the glycidic ester of the formula (IV). If the Lewis acid is used in an amount of less than the equi-molar proportion to the glycidic ester, a part of the glycidic ester remains unreacted. The solvent in which the reaction of the glycidic ester of the formula (IV) with Lewis acid takes place is not critical, as long as it is an aprotoic, polar solvent. However, the solvent may conveniently be dimethylsulfoxide or dimethylformamide when boron trifluoride is used as the Lewis acid. The solvent may suitably be an ether of a relatively high-boiling point such as isopropylether. The reaction of the glycidic ester of the formula (IV) with Lewis acid may preferably be carried out at a reaction temperature of about 0°C to about 100°C for a reaction time of about 30 minutes to 1 hour. The 2-hydroxy-3-(4-alkylphenyl)-3-butenoic acid ester of the formula (II) so obtained may be isolated from the reaction mixture and then be purified in a facile way.

The 2-hydroxy-3-(4-alkylphenyl)-3-butenoic acid ester of the formula (II) is a new substance and is useful as a starting material or intermediate product for the production of the 2-(4-alkylphenyl)-propionic acid of the formula (I) which is a valuable anti-inflammatory agent. According to a second aspect of this invention, therefore, there is provided as the new compound a 2-hydroxy-3-(4-alkylphenyl)-3-butenoic acid ester of the formula (II):

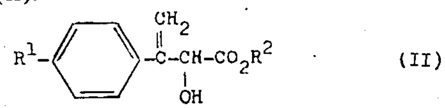

wherein $R^1$ is an alkyl group of 2–4 carbon atoms and $R^2$ is an alkyl group of 1–3 carbon atoms. Methyl 2-hydroxy-3-(4-isobutylphenyl)-3-butenoate (in the formula (II): $R^1$=isobutyl, $R^2$=methyl) is an oily substance which is heat-stable and of which infra-red absorption spectrum exhibits main peaks at 3480, 1740 and 860 $cm^{-1}$. Nuclear magnetic resonance spectrum thereof shows main absorption peaks at δ=0.86 (6H. d), 2.42 (2H. d), 3.57 (3H. s) and 4.91 (1H. s).

According to a third aspect of this invention, there is further provided a process for the production of a 2-hydroxy-3-(4-alkylphenyl)-3-butenoic acid ester of the formula (II):

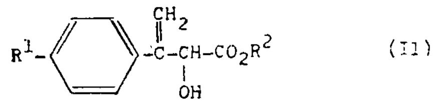

wherein $R^1$ is an alkyl group of 2–4 carbon atoms and $R^2$ is an alkyl group of 1–3 carbon atoms, which comprises reacting a glycidic ester of the formula (IV):

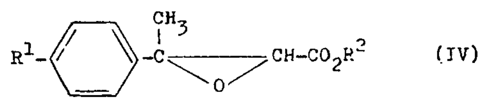

wherein $R^1$ and $R^2$ have the same meanings as defined above, with a Lewis acid in an aprotoic, polar solvent.

The 3-methyl-3-(4-alkylphenyl)-pyruvic acid of the formula (III) and the 3-methyl-3-(4-alkylphenyl)-pyruvate of the formula (X) are obtained as the intermediate products in the first aspect process of this invention and, as mentioned before, are new substances which are useful for the production of the valuable anti-inflammatory compound 2-(4-alkylphenyl)-propionic acid. According to a further aspect of this invention, therefore, there is provided a 3-methyl-3-(4-alkylphenyl)-pyruvic acid compound of the formula (III):

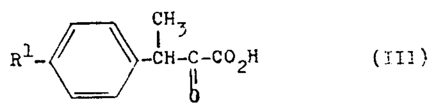

wherein $R^1$ is an alkyl group of 2–4 carbon atoms. 3-Methyl-3-(4-isobutylphenyl)-pyruvic acid (in the formula (III); $R^1$=isobutyl) has the following properties: Colorless needle-like crystal of a melting point of 60.0°–61.4°C. Infra-red absorption spectrum: main peak at 1710, 1380 and 790 $cm^{-1}$. Nuclear magnetic resonance spectrum (ppm.) δ = 0.86 (6H.d), 1.45 (3H.d), 2.43 (2H.d) and 4.65 (1H.q).

Elemental analysis: Calculated for $C_{14}H_{18}O_3$: C 71.77%, H 7.74%; Found: C 71.54%, H 7.87%.

The 2-hydroxy-3-(4-alkylphenyl)-3-butenoic acid ester of the formula (II) which is used as the starting compound in the first aspect process of this invention may also be prepared in another way, for example, by ring-opening the glycidic ester of the above-mentioned formula (IV) through a treatment with a diluted mineral acid in tetrahydrofuran to produce a di-ol derivative of the formula (V):

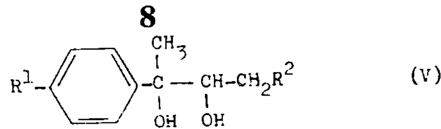

wherein $R^1$ and $R^2$ have the same meanings as defined above, which is then dehydrated through a treatment with p-toluenesulfonic acid in xylene.

The invention is now illustrated with reference to the following Examples to which this invention is not limited.

EXAMPLE 1

Preparation of methyl 2-hydroxy-3-(4-isobutylphenyl)-3-butenoate.

To a stirred mixture of 54.0 g. of 4-isobutylacetophenone and 65.0 g. of methyl chloroacetate was slowly added 30.0 g. of sodium methoxide over 3 hours at a temperature of not more than 5°C under nitrogen atmosphere. The mixture was allowed to be raised to ambient temperature and stirred overnight. The mixture was then heated to a temperature of 80°–90°C and agitated at this temperature for 1.5 hours. After cooling, the reaction mixture was admixed with ethyl ether, washed with water, dried over anhydrous sodium sulfate and distilled to remove the ether. The residue was distilled to afford 61.0 g. of methyl 3-methyl-3-(4-isobutylphenyl)-glycidate. bp. 108°–112°C/0.2 mm Hg. Yield 80.0% (based on the theoretical).

The methyl 3-methyl-3-(4-isobutylphenyl)-glycidate (7.44 g) was dissolved in 30 ml of dry dimethylsulfoxide, and the solution was admixed with 5 ml of a solution of 47% boron trifluoride in ethyl ether under ice-cooling. The mixture was allowed to stand at ambient temperature for 2 hours and then poured into a volume of water. The aqueous mixture was extracted with ethyl ether and the ether extract was washed successively with water, aqueous sodium hydrogen carbonate, water and a saturated aqueous solution of sodium chloride and then was dried over anhydrous magnesium sulfate. The ethyl ether was distilled off under reduced pressure, and the residue was distilled to give 6.6 g. of the desired compound. bp. 113°–115°C/0.2 mmHg. Yield 88% (based on the theoretical).

Elemental analysis: Calculated for $C_{15}H_{20}O_3$; C 72.55, H 8.12%; Found; C 71.99, H 8.18%.

EXAMPLE 2

Preparation of ethyl 2-hydroxy-3-(4-t-butylphenyl)-3-butenoate.

To a stirred mixture of 26.4 g. of 4-t-butylacetophenone and 16.2 g. of ethyl chloroacetate was slowly added 10.2 g. of sodium ethoxide over 30 minutes at a temperature of 10°–15°C. The mixture was allowed to be raised to room temperature and stirred overnight at room temperature and then heated to 85°C., followed by further stirring at this temperature for 1.5 hours. After cooling, the reaction mixture was admixed with ethyl ether, washed with water, dried over anhydrous magnesium sulfate and distilled to remove the ethyl ether. Distillation of the residue gave 25.0 g. of ethyl 3-methyl-3-(4-t-butylphenyl)-glycidate. bp. 108°–111°C/0.2 mmHg. Yield 67% (based on the theoretical).

The ethyl 3-methyl-3-(4-t-butylphenyl)-glycidate (7.86 g) was taken up into 30 ml of dry dimethylformamide and the solution was admixed with 5 ml of a solution of 47% boron trifluoride in ethyl ether under ice-cooling. The mixture was subsequently processed in the same manner as in Example 1 to afford 6.30 g. of the desired compound. bp. 115°–119°C/0.2 mmHg. Yield 80% (based on the theoretical).

Elemental analysis: Calculated for $C_{16}H_{22}O_3$; C 73.25, H 8.45%; Found; C 72.91, H 8.60%.

EXAMPLE 3

Preparation of isopropyl 2-hydroxy-3-(4-isobutylphenyl)-3-butenoate.

Isopropyl 3-methyl-3-(4-isobutylphenyl)-glycidate (8.28 g) was dissolved in 30 ml of dry dimethylacetoamide and the solution so obtained was admixed with 5 ml of a solution of 47% boron trifluoride in ethyl ether under ice-cooling. The mixture was subsequently processed in the same manner as in Example 1 to give 7.0 g. of the desired compound. bp. 122°–124°C/0.2 mmHg. Yield 85% (based on the theoretical):

Elemental analysis: Calculated for $C_{17}H_{24}O_3$; C 73.88, H 8.75%; Found; C 74.01, H 8.91%.

EXAMPLE 4

Preparation of methyl 2-hydroxy-3-(4-isobutylphenyl)-3-butenoate.

To a solution of 10.0 g. of aluminum chloride in 100 ml of isopropyl ether was added dropwise a solution of 10.0 g. of methyl 3-methyl-3-(4-isobutylphenyl)-glycidate in 40 ml of isopropyl ether under stirring. After the addition completed, the admixture was stirred for 3.5 hours under reflux. After cooling, the reaction mixture was admixed with a diluted hydrochloric acid and then stirred for 20 minutes. The mixture was allowed to stand so that it was separated into the isopropyl ether phase and the aqueous phase. The isopropyl ether phase was removed and the aqueous phase was extracted with isopropyl ether. The isopropyl ether extract so obtained was combined together with the aforesaid isopropyl ether phase, and the combined solution was washed successively with water, aqueous sodium hydrogen carbonate and water and then dried over anhydrous magnesium sulfate. The solution was distilled under reduced pressure to remove the isopropyl ether. Distillation of the residue gave 6.7 g. of methyl 2-hydroxy-3-(4-isobutylphenyl)-3-butenoate. bp. 113°–115°C/0.2 mmHg. Yield 67.0 % (based on the theoretical).

Elemental analysis: Calculated for $C_{15}H_{20}O_3$: C 72.55, H 8.12%; Found; C 72.18, H 7.96%.

EXAMPLE 5

Synthesis of 2-(4isobutylphenyl)-propionic acid.

i. Production of 3-methyl-3-(4-isobutylphenyl)-pyruvic acid.

Methyl 2-hydroxy-3-(4-isobutylphenyl)-3-butenoate (5.8 g) was dissolved in 10 ml of anhydrous methanol and the solution so obtained admixed with a solution of sodium methylate which had been prepared by dissolving 0.54 g. of metallic sodium into 30 ml of anhydrous methanol. The admixture was heated for 20 minutes under reflux to effect the conversion of the 2-hydroxy-3-(4-isobutylphenyl)-3-butenoate into the 3-methyl-3-(4-isobutylphenyl)-pyruvate. The reaction mixture was then admixed with water and again heated for 10 minutes under reflux to effect the hydrolysis of the pyruvate product. The reaction mixture was subsequently distilled under reduced pressure to remove the methanol, and the residue was taken up into water. The insoluble oil was removed by extracting with ethyl ether. The resulting aqueous layer (solution) was acidified by addition of hydrochloric acid and then extracted with ethyl ether. The ether extract was washed with water, dired over anhydrous magnesium sulfate and then distilled under reduced pressure to remove the ethyl ether. A crude crystalline product was obtained as the residue and recrystallised from petroleum benzine to give 4.5 g. of 3-methyl-3-(4-isobutylphenyl)-pyruvic acid. mp. 60.0°–61.4°C. Yield 82% (based on the theoretical).

Elemental analysis: Calculated for $C_{14}H_{18}O_3$; C 71.77, H 7.74%; Found; C 71.54, H 7.87%.

ii. Production of 2-(4-isobutylphenyl)-propionic acid.

3-Methyl-3-(4-isobutylphenyl)-pyruvic acid (7.1 g) obtained in the above procedure of Example 5(i) was dissolved in 50 ml of an aqueous solution of 8% sodium hydroxide. To the resulting solution was added dropwise 4.5 ml of an aqueous solution of 30% hydrogen peroxide under ice-cooling and stirring. The mixture was allowed to be raised to room temperature and then stirred overnight at room temperature. The reaction mixture was then acidified by addition of hydrochloric acid and subsequently extracted with ethyl ether. The ether extract was washed with water, dried over anhydrous magnesium sulfate and then distilled under reduced pressure. Recrystallisation of the crude crystalline product so obtained from petroleum benzine gave 5.1 g. of 2-(4-isobutylphenyl)-propionic acid. mp. 75.0°–76.5°C. Yield 82%.

Elemental analysis: Calculated for $C_{13}H_{18}O_2$; C 75.69, H 8.80%; Found; C 75.70, H 9.04%.

EXAMPLE 6

Synthesis of 2-methyl-3-(4-t-butylphenyl)-propionic acid.

i. Production of 3-methyl-3-(4-t-butylphenyl)-pyruvic acid.

Ethyl 2-hydroxy-3-(4-t-butylphenyl)-3-butenoate (5.24 g) was dissolved in 10 ml of anhydrous ethanol and the solution so obtained was admixed with a solution of potassium ethylate which had been prepared by dissolving 0.78 g. of metallic potassium in 30 ml of anhydrous ethanol. The admixture was heated for 20 minutes under reflux. To the reaction mixture was added water, and the mixture was again heated for 10 minutes under reflux. The reaction mixture was distilled under reduced pressure to remove the ethanol. The residue was admixed with water and the insoluble oil was removed by extracting with ethyl ether. The aqueous phase (solution) was acidified with hydrochloric acid and then extracted with ethyl ether. The ether extract was washed with water, dried over anhydrous magnesium sulfate and distilled under reduced pressure to remove the ethyl ether. A crude crystalline product was obtained as the residue and recrystallised from petroleum benzine, affording 3.8 g. of 3-methyl-3-(4-t-butylphenyl)-pyruvic acid. mp. 81.1°–82.9°C. Yield 81% (based on the theoretical).

Elemental analysis: Calculated for $C_{14}H_{18}O_3$; C 71.77, H 7.74%; Found; C 71.68, H 7.69%.

ii. Production of 2-(4-t-butylphenyl)-propionic acid.

3-Methyl-3-(4-t-butylphenyl)-pyruvic acid (3.8 g) obtained in the above procedure of Example 6(i) was admixed with 30 ml of an aqueous solution of 8% sodium hydroxide and 2.5 ml of aqueous 30% hydrogen peroxide and the mixture was processed in the same manner as in Example 5(ii) to give 2.9 g. of 2-(4-t-butylphenyl)-propionic acid. mp. 100.5°–102.8°C. Yield 87%.

Elemental analysis: Calculated for $C_{13}H_{18}O_2$; C 75.69, H 8.80%; Found; C 75.61, H 8.86%.

EXAMPLE 7

Synthesis of 2-(4-isobutylphenyl)-propionic acid.

i. Production of 3-methyl-3-(4-isobutylphenyl)-pyruvic acid.

Methyl 3-methyl-3-(4-isobutylphenyl)-pyruvate (8.1 g) was dissolved in 50 ml of methanol and the solution was admixed with 10 ml of an aqueous solution of 10% sodium hydroxide, and the mixture was heated for 40 minutes under reflux to effect the hydrolysis. The reaction mixture was distilled under reduced pressure to remove the methanol. The residue was taken up into water and the insoluble oil was removed by extracting with ethyl ether. The aqueous solution so obtained was acidified by addition of hydrochloric acid and then extracted with ethyl ether. The ether extract was washed with water, dried over anhydrous sodium sulfate and distilled under reduced pressure to remove the ether. A crude crystalline product was obtained as the residue and recrystallised from petroleum benzine to give 7.1 g. of 3-methyl-3-(4-isobutylphenyl)-pyruvic acid. mp. 60.5°–61.5°C. Yield 93%.

Elemental analysis: Calculated for $C_{14}H_{18}O_3$; C 71.77, H 7.74%; Found; C 71.73, H 7.59%.

ii. Production of 2-(4-isobutylphenyl)-propionic acid.

The procedure of Example 5(ii) was repeated using 7.1 g. of 3-methyl-3-(4-isobutylphenyl)-pyruvic acid obtained in Example 7(i), 50 ml of aqueous 8% sodium hydroxide and 4.5 ml of 30% aqueous hydrogen peroxide. 4.9 g. of 2-(4-isobutylphenyl)-propionic acid was afforded. mp. 75.0°–76.5°C. Yield 78% (based on the theoretical).

Elemental analysis: Calculated for $C_{13}H_{18}O_2$; C 75.69, H 8.80%; Found; C 76.80, H 8.75%.

The preceeding examples can be repeated with similar success by substituting the generically or specifically described reactants and/or operating conditions of this invention for those used in the preceeding examples.

From the foregoing description, one skilled in the art can acertain the essential characteristics of this invention, and without departing from the spirit and scope thereof, can make various changes and modifications of the invention to adapt it to various usage conditions.

What we claim is:

1. A 2-hydroxy-3-(4-alkylphenyl)-3-butenoic acid ester of the formula

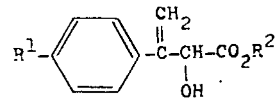

wherein $R^1$ is an alkyl group of 2–4 carbon atoms and $R^2$ is an alkyl group of 1–3 carbon atoms.

2. A process for the production of a 2-hydroxy-3-(4-alkylphenyl)-3-butenoic acid ester of the formula (II):

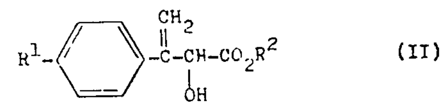

wherein $R^1$ is an alkyl group of 2–4 carbon atoms and $R^2$ is an alkyl group of 1–3 carbon atoms, which comprises reacting a glycidic ester of the formula (IV):

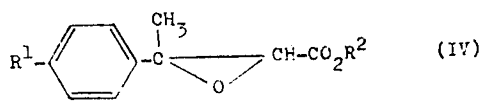

wherein $R^1$ and $R^2$ have the same meanings as defined above, with a Lewis acid in an aprotic, polar solvent.

* * * * *